United States Patent [19]

Audeh et al.

[11] 4,250,739
[45] Feb. 17, 1981

[54] APPARATUS AND METHOD FOR TBP-DISTILLATION OF CRUDE OIL

[75] Inventors: Costandi A. Audeh, Princeton; Richard N. Lovett, Woodbury, both of N.J.

[73] Assignee: Mobil Oil Corporation, Fairfax, Va.

[21] Appl. No.: 72,741

[22] Filed: Sep. 4, 1979

[51] Int. Cl.³ .................... G01N 25/08; G01N 25/14
[52] U.S. Cl. ................................... 73/17 A; 364/501
[58] Field of Search ............ 73/17 A, 61.3; 196/132; 364/501; 203/2; 208/366

[56] References Cited

U.S. PATENT DOCUMENTS

| | | | |
|---|---|---|---|
| 3,239,432 | 3/1966 | Rhodes et al. | 73/17 |
| 3,364,731 | 1/1968 | Hook | 73/61.3 |
| 3,732,723 | 5/1973 | Goolsby et al. | 73/17 |

Primary Examiner—Herbert Goldstein
Attorney, Agent, or Firm—C. A. Huggett; V. J. Frilette

[57] ABSTRACT

Provided herein is a novel method for generating TBP-distillation curves for crude petroleum oils, which curves are free of the large discontinuity in the raw data that is commonly observed when vacuum distillation is begun. The temperature-incremental volume data is accumulated up to a temperature equivalent to about 650° F. at 760 mm. to provide a data bank. The data bank is then used to compute expected yield-temperature values up to a temperature equivalent of 850° F. at 760 mm. The atmospheric residuum is then vacuum distilled and actual yield-temperature datum is compared with expected valves to obtain a deviation. The vacuum is then adjusted to reduce the deviation. Provided also is an automated apparatus for generating such curves.

5 Claims, 2 Drawing Figures

APPARATUS AND METHOD FOR TBP-DISTILLATION OF CRUDE OIL

BACKGROUND OF THE INVENTION

1. Field of the Invention

This invention is concerned with the generation of true boiling point curves for petroleum crude oils. In particular, it is concerned with a novel vacuum distillation apparatus and method of use thereof which eliminates in reproducible manner the discontinuity usually observed with the raw distillation data at the point at which high vacuum distillation begins.

2. Description of the Prior Art

The first major process in refining crude petroleum is fractional distillation to separate the crude into various boiling range cuts. Crudes differ widely in the amount of material that may be recovered having any specified boiling range. Thus, some crudes may contain as much as 75 vol.% straight-run gasoline, while others contain 10 vol.% or less.

It is of considerable importance to design engineers concerned with the design of distillation equipment to know beforehand the boiling point-yield character of the crude oils expected to be processed at a particular refinery. And, needless to say, boiling point-yield characteristics are critically considered in the purchase and trading of crudes.

Petroleum engineers have developed an assay technique for characterizing a crude that permits them to predict how that crude will behave in a particular refinery distillation. This technique requires that a sample of the crude be subject to analytical distillation under prescribed conditions in the laboratory. The first stage of the distillation is made in an atmospheric pressure still, and the temperature required to accumulate incremental fractions, usually about 2% to 4% of the total crude charge, is noted. A nominal vacuum of about 10 mm is commonly applied after the gasoline cut point of about 425° F. is reached to avoid excessive pot temperatures. This stage of the distillation is terminated at about the temperature at which the crude begins to crack, i.e. undergo thermal changes, which is a temperature in the range of about 625° to 725° F., and usually about 650° F. The termination temperature is determined by the operator, and based on prior knowledge of the nature of the crude type that is being evaluated. After terminating the atmospheric distillation, the reduced crude, or atmospheric residuum, as it is commonly called, is transferred to a vacuum distillation apparatus and the distillation continued under high vacuum, for example, at a pressure of about 200 microns. Each temperature required for the accumulation under vacuum of an increment of distillate is transformed by computation to the temperature that would have been observed at atmospheric pressure were not the crude subject to thermal degradation. This computation of course involves an assumption about the temperature-vapor pressure relationship of the incremental fractions. The vacuum distillation is terminated at about 1050° F., at which point about all of the practically recoverable distillate oil has been taken overhead.

The procedure hereinabove described permits the operator to construct a boiling-point yield curve over the entire distillation range and in terms of temperatures all referred to atmospheric pressure. Such curves are known as "true boiling point distillation curves", or simply "TBP curves", and the distillation procedure as a "TBP distillation". A description of useful apparatus is given in A.S.T.M. Method D2892, titled "Distillation of Crude Petroleum", published by the American Society for Testing Materials, Philadelphia, Pa., and is incorporated herein by reference.

The manner in which TBP distillations are presently conducted usually results in a large discontinuity of the raw data, computed at 760 mm pressure, at the point at which vacuum distillation begins. Such a discontinuity is illustrated by FIG. 1 of the drawing. The portion of the curve up to 650° F. is exemplary of a plot for the raw 760 mm data from the atmospheric still. The remainder is exemplary for the vacuum distillation. The first increment of vacuum distillate, the increment noted in FIG. 1 as between A and B, is recovered at a temperature much higher than would be expected from an extrapolation of the atmospheric distillation curve. This aberration, herein called a discontinuity, often persists in progressively lesser degree for later increments of distillate until a temperature equivalent to about 850° F. at 760° mm is reached.

There are two known methods for obtaining TBP curves which reduce or eliminate the discontinuity on changing from nominally atmospheric to high vacuum condition. One of these is to blend back a number of the last increments of atmospheric distillate with the atmospheric residuum prior to initiating vacuum distillation. This method is cumbersome and costly. The other method, more commonly practiced, is for the operator to "adjust" the data points and thus force a continuity on the curve. The latter method leaves much to be desired since the "adjustments" are at least to some extent arbitrary, and in some cases require a repetition of the distillation before adjustments can be made with confidence. Thus, the TBP curve prepared by one operator often will not be exactly like the curve prepared by another operator using identical raw data. Unfortunately, these arbitrary adjustments are made in a region of the distillation where important refinery cut points are set.

At this point we wish to note that TBP curves are not intended to precisely simulate refinery operation. Rather, they provide the engineer with a tool which he uses, together with his prior experience, to predict or estimate how a particular crude will behave in an existing refinery or in a distillation unit of particular design. That this tool is imprecise to the extent that it incorporates an element of uncertainty is evident from the foregoing description. It is an object of this invention to provide an improved method for determining the TBP curve of a crude oil. It is a further object of this invention to provide an improved apparatus for vacuum assay of reduced crudes. These and other objects will be evident to those skilled in the art on reading this entire specification including the claims thereof.

DESCRIPTION OF THE INVENTION

Figure 1:
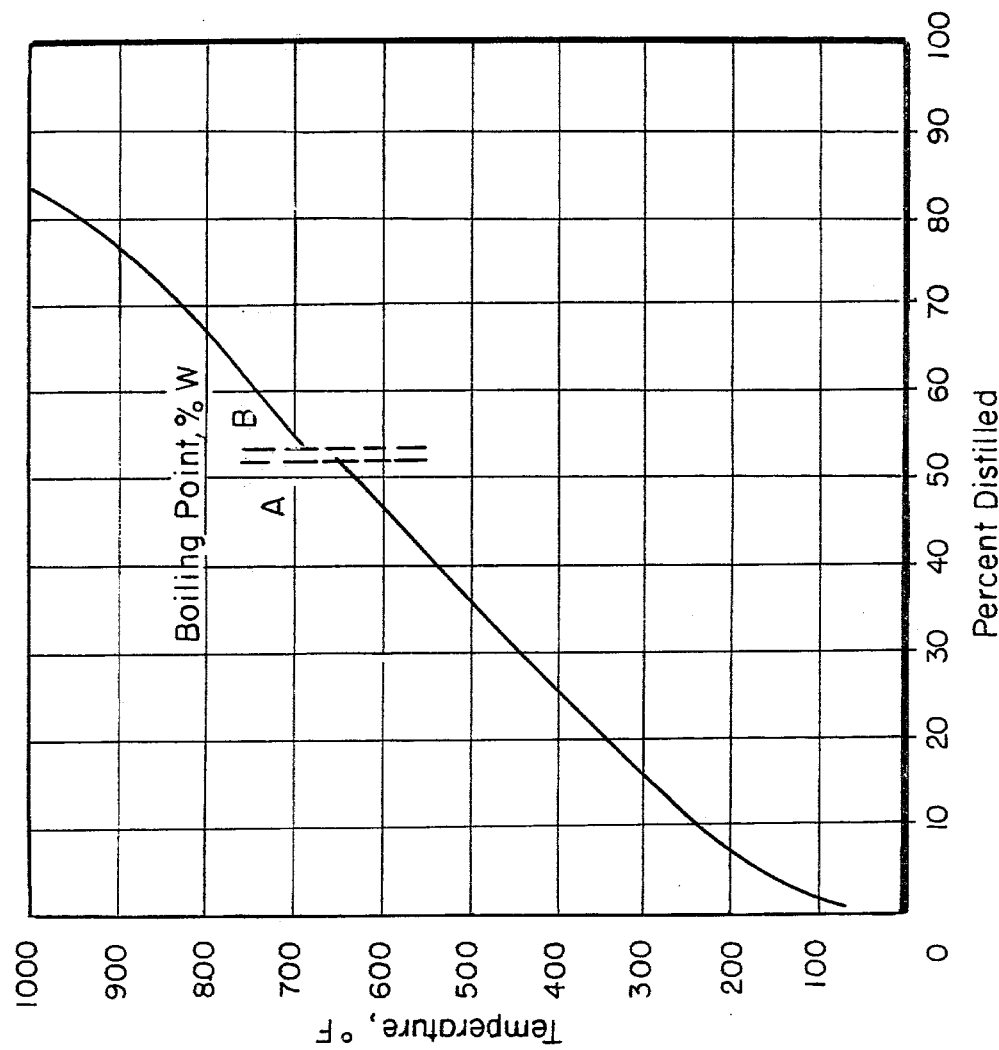
FIG. 1—Illustrates discontinuity of the data
FIG. 2—Crude Assay High Vacuum Still

In the method of the present invention, the temperature-incremental volume data for the nominally atmospheric portion of the distillation of a particular crude is accumulated in essentially the usual manner. This data, for convenience, will be referred to herein as the data bank for that crude. This data bank is used to compute or estimate a best-fit curve for the substantially linear portion of the cumulative volume data which usually is observed at temperatures from about 250° F. to about 650° F. This best-fit curve is preferably obtained by the least squares estimate of the best-fit straight line or the best-fit second-order equation, as described for example in "Statistical Methods in Research and Production", pp. 194 and 215, Edited by Owen L. Davies, Hafner Publishing Co., New York, N.Y. (1961). The best fit line or curve is extrapolated to about 850° F. to provide a continuum of expected temperature-cumulative yield data points. With this preparation completed, the vacuum distillation is initiated and monitored to obtain an actual temperature-yield datum point. This actual datum point is compared with the expected datum point to determine the deviation therefrom. The vacuum is then adjusted in a direction to reduce said deviation. It is preferred to simultaneously adjust the rate of heating in a direction to reduce said deviation. Following one or both of said adjustments, it is preferred to obtain a second actual temperature-yield datum point, compare this with the expected datum point, and make a second adjustment of the vacuum in a direction to reduce the observed deviation. The rate of heating, optionally, also is adjusted. This sequence of steps preferably is reiterated until a vapor temperature equivalent to about 850° F. at 760 mm is reached, at which point the distillation is continued in the conventional fashion up to a vapor temperature of about 1050° F., at which temperature all of the practically distillable oil has passed overhead. Optionally, the iteration is discontinued at a temperature less than 850° F. if no significant deviation is observed at the lesser temperature. By the method of this invention a TBP curve based on raw data adjusted to 760 mm and substantially without discontinuity is obtained.

The method of this invention may be used to advantage by any skilled operator. However, it is particularly well suited for use with the novel modified vacuum distillation apparatus hereinbelow described.

Any high vacuum distillation apparatus suitable for crude assay may be automated to perform the operations hereinabove described. Since suitable stills already provide a measure of the distillation temperature as for example by thermocouple, and a measure of the vacuum, an automatic or semi-automatic measure of the volume of distillate is all that is needed to supply the raw distillation data and correct it to 760 mm. This information, passed to a data processor provided with a library consisting of the data bank and one or more simple programs, generates a deviation signal to adjust the vacuum with or without adjustment of the rate of heating.

Figure 2:
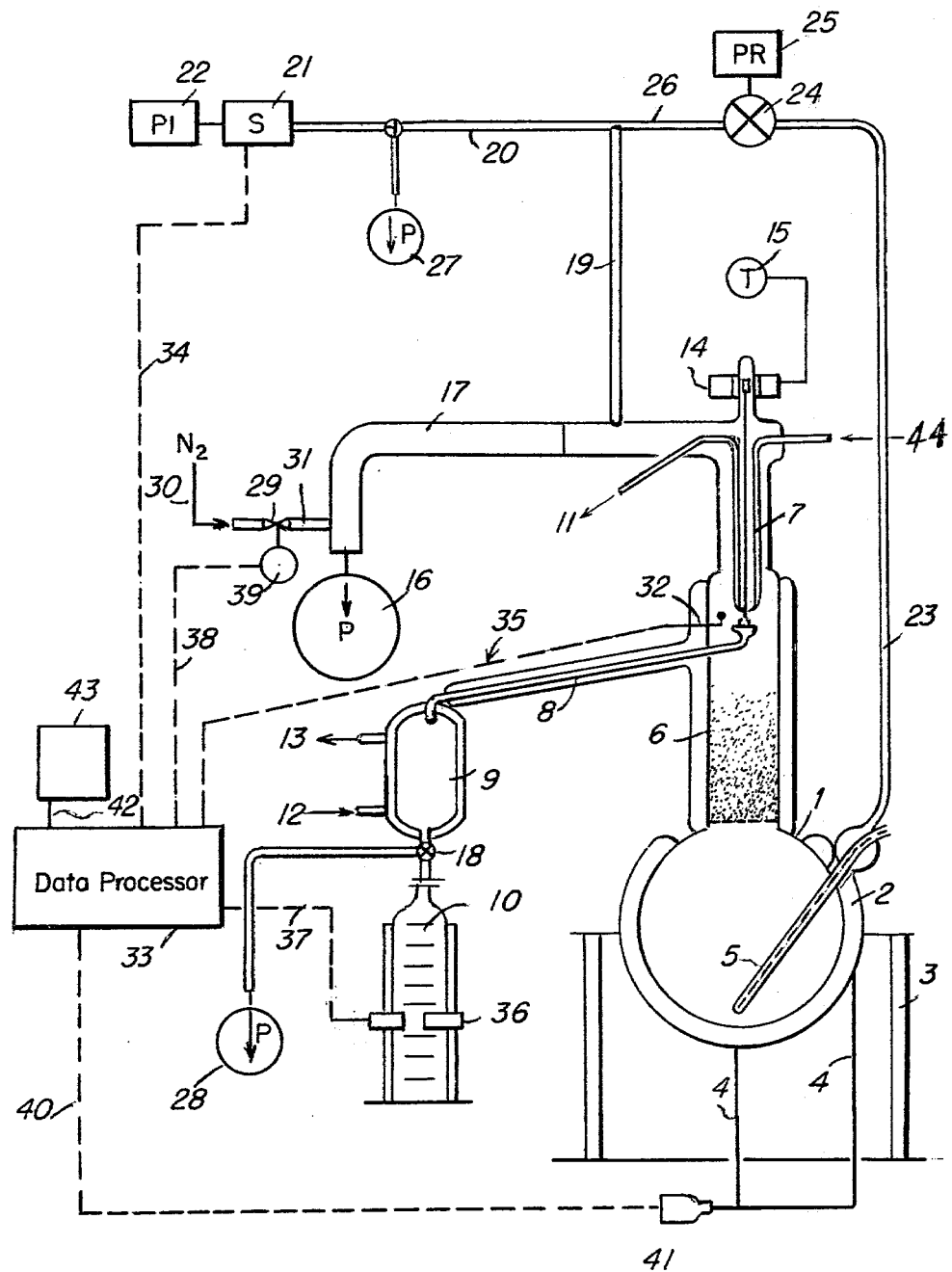

FIG. 2 of the drawing illustrates modification of a suitable vacuum still to provide automated control of the distillation in accordance with this invention.

The conventional elements will now be described. A glass still pot of about 12 liter capacity (1) is provided with a heating mantle (2) connected to electric power leads (4). The assembly is supported on frame (3). The still pot (1) is provided with a thermocouple well (5) to permit measurement of the temperature in the still pot. The still pot (1) communicates with vacuum fractionating column (6), which may be about 8 inches long and may have an inner diameter of about 4 inches. The fractionating column (6) is in communication with reflux condenser (7). Condensate transfer tube (8) permits withdrawal of condensate from fractionating column (6) and delivery to cutter (9). Fractionating column (6) and transfer tube (8) preferably are vacuum jacketed as shown. Provisions for cooling are provided for the condenser and cutter via lines (44), (11), (12) and (13). A solenoid valve (14) and timer (15) permit control of the condensate withdrawal rate or reflux ratio. The working vacuum is provided by still vacuum pump (16), which may be of the Kinney type. The working vacuum is communicated to fractionating column (6) and pot (1) by vacuum line (17), which may have an inner diameter of about 1½ inches. Valve (18) permits transfer of the cooled condensate in cutter (9) to receiver (10). The pressure in line (17) is communicated via tube (19) and tube (20) to a vacuum sensor (21) which generates a signal which activates pressure indicator (22). Pressure sensor (21) and indicator (22) may be components of a datametrics electronic manometer. The level of vacuum in the still pot (1) is communicated via tube (23) to differential pressure cell (24), wherein it is compared with the pressure in line (17) communicated via line (19) and line (26). The pressure difference recorder (25) is operated by the differential pressure cell (24). Auxiliary vacuum pump (27) assists in the initial start-up of the unit, and auxiliary vacuum pump (28) serves to evacuate the receiver (10) whenever this is changed. The vacuum in the system may be reduced or eliminated by manually manipulating valve (29), which permits nitrogen to enter via line (30) and (31). Temperature measuring means (32) is provided in the vapor space of fractionating column (6). Such means include a thermocouple or a thermistor.

For purposes of the present invention, the apparatus is provided with a data processor (33), which may be a mini computer. The data processor is provided with a data bank and programs, as needed, to compare actual temperature yield relationships with expected values. A signal indicative of the effective vacuum in the system, and which is generated by sensor (21) is placed on line (34) and passed to the data processor (33). A signal generated by temperature measuring means (32) is placed on line (35) and passed to data processor (33). A liquid volume or liquid mass sensing device (36), such as a photoelectric sensor, places a signal indicative of the amount of liquid in receiver (10) on line (37) whence it is passed to data processor (33). The data processor, either at prescribed intervals or substantially continuously generates a signal indicative of the deviation of the real data from the expected data, and places this on line (38) which is communicated to controller (39) which automatically controls valve (29) to adjust the vacuum in a direction to reduce said deviation. A signal indicative of the deviation generated by the data processor may be placed on line (40) whence it is communicated to heat input controller (41) which adjusts the rate of heat input in response to said signal and in a direction to reduce said deviation. The signals placed on line (38) and on line (40) may be the same, or they may be different depending on the extent of the deviation. The data processor is programmed in such a manner that the deviation is automatically reduced to zero when thermocouple (32) indicates a temperature of 850° F. or higher. During the course of the distillation, the data processor (33) generates a signal indicative of the temperature-volume relationship, preferably corrected to 760 mm pressure and places the signal on line (42) whence it is passed to (43), which may be either an indicator or a recorder.

It will be obvious to those skilled in the art that the present invention, while particularly applicable to crude petroleum oils, may equally well be used for other hydrocarbon oils which contain a very heavy fraction with or without a residue. Oils derived from tar sands, liquified coal, and similar materials may be assayed by the method in the apparatus of this invention. Similarly, variations in the method for predicting vacuum data may be made, such as the use of probability paper or regressions based on a probability relationship, may be substituted for the simple linear coordinate relationship hereinabove described. It is well known to those skilled in the art that TBP curves are linear over a broader range of temperature when plotted on probability paper compared with simple graph paper. Furthermore, it will be evident to those skilled in the art that the present invention may be used effectively to initiate the vacuum distillation at a lower cut point than the usual temperature of about 650° F., thereby obviating the slowdown in distillation that is often observed in the atmospheric portion of the distillation as one approaches its terminal portion. These and other variants are contemplated as within the scope of the present invention and are to be considered a part of it.

What is claimed is:

1. An improved method for determining the TBP distillation curve of a petroleum crude oil, which method comprises: distilling said crude oil at or near atmospheric pressure and up to a temperature equivalent to about 650° F. at 760 mm thereby forming an atmospheric residuum of said crude oil, and accumulating temperature-incremental volume data during said atmospheric pressure distillation thereby providing a data bank; establishing from said data bank the expected yield-temperature relationship up to a temperature equivalent to about 850° F. at 760 mm; vacuum distilling the first incremental volume of distillate from said atmospheric residuum; comparing at 760 mm the actual yield-temperature datum with the expected value to derive the deviation therefrom; and adjusting the vacuum in a direction to reduce said deviation.

2. The method described in claim 1 wherein said steps of distilling an incremental volume of distillate; comparing for that increment the actual and expected yield-temperature data to derive a deviation therefrom; and adjusting the vacuum in a direction to reduce the deviation; are reiterated for subsequent incremental volumes of vacuum distillate until a distillate vapor temperature equivalent to about 850° F. at 760 mm is reached.

3. The method described in claim 1 or in claim 2 wherein the rate of heating of the still pot also is adjusted in a direction to reduce said deviation.

4. In a vacuum still suitable for the TBP distillation of the atmospheric residuum of a crude petroleum oil, said crude oil being characterized by a data bank obtained by distillation at or near atmospheric pressure and up to a temperature equivalent to about 650° F. at 760 mm said still comprising a still pot for charging said residuum, controllable heating means for heating and vaporizing said residuum, fractionating means for fractionating said vapor, condensing means for converting said fractionated vapor to distillate, receiving means for collecting said distillate, means for maintaining a controlled high vacuum in said still, and temperature-measuring means associated with said fractionating means for generating a signal indicative of the temperature of said fractionated vapor, the improvement comprising including in said system volume-measuring means associated with said receiving means for generating a signal indicative of the distillate volum, means for comparing said temperature and volume signals with a set of expected values computed from said data bank to generate a signal indicative of the deviation from said expected values, and means responsive to said deviation signal for adjusting and controlled high vacuum in a direction to reduce said deviation.

5. The apparatus described in claim 4 wherein is included means responsive to said deviation signal for adjusting said controllable heating means in a direction to reduce said deviation.

* * * * *